United States Patent [19]

Yamada et al.

[11] Patent Number: 4,546,081

[45] Date of Patent: Oct. 8, 1985

[54] CONTINUOUS ALCOHOL FERMENTATION PROCESS USING IMMOBILIZED YEAST

[75] Inventors: Tomiaki Yamada, Yokohama; Tsuneo Sazanami, Yokosuka; Keiichiro Watanabe, Yokohama; Takamitsu Iida; Eiichi Hasegawa, both of Hiratsuka; Masahiro Sakamoto, Kanagawa, all of Japan

[73] Assignees: JGC Corporation, Tokyo; Kansai Paint Co., Ltd., Amagasaki, both of Japan

[21] Appl. No.: 499,172

[22] Filed: Jun. 1, 1983

Related U.S. Application Data

[63] Continuation of Ser. No. 267,817, May 27, 1981, abandoned.

[30] Foreign Application Priority Data

May 30, 1980 [JP] Japan ................... 55-72586

[51] Int. Cl.⁴ ................. C12P 7/06; C12N 11/12; C12N 11/08; C12N 11/04
[52] U.S. Cl. .................... 435/161; 435/179; 435/180; 435/182
[58] Field of Search ............ 435/161, 162, 165, 174, 435/178, 179, 180, 182; 426/11

[56] References Cited

U.S. PATENT DOCUMENTS

| 3,402,103 | 9/1968 | Amberg et al. | 435/161 X |
| 3,767,790 | 10/1973 | Guttag | 435/182 X |
| 3,972,776 | 8/1976 | Vieth et al. | 435/177 |
| 4,051,011 | 9/1977 | Miyauchi et al. | 435/288 X |
| 4,287,176 | 9/1981 | Demchak et al. | 424/270 |
| 4,355,108 | 10/1982 | Gaddy et al. | 435/165 |
| 4,427,775 | 1/1984 | Chen et al. | 435/161 |

FOREIGN PATENT DOCUMENTS 42530 3/1980 Japan ................... 435/182

OTHER PUBLICATIONS

Chibata et al., "Kagaku Kozyo", vol. 23, No. 3, Published by Nikkan Kogyo Shinbun Sha prior to 1980, (pp. 26–30).

Primary Examiner—David M. Naff
Attorney, Agent, or Firm—Flynn, Thiel, Boutell & Tanis

[57] ABSTRACT

Continuous fermentation with yeast to produce alcohol is carried out by continuously passing a carbohydrate-containing substrate liquid through a vessel packed with a thin film means having yeast immobilized therein. Surfaces of the thin film means extend in the direction of flow within the vessel to provide elongated parallel passages. The thin film means occupies from 10 to 65% of the volume of the vessel and preferably has a thickness of 0.1 to 3 mm. Preferably, the thin film means is formed by mixing an aqueous yeast suspension with a photo-crosslinkable resin and subjecting the mixture to radiation to photo-crosslink the resin.

7 Claims, 2 Drawing Figures

CONTINUOUS ALCOHOL FERMENTATION PROCESS USING IMMOBILIZED YEAST

This application is a continuation of U.S. Pat. No. 267,817, filed May 27, 1981, now abandoned.

BACKGROUND OF THE INVENTION (a) Field of the Invention

The present invention relates to a continuous alcohol fermentation process using an immobilized yeast, in particular a continuous alcohol fermentation process which is so designed that a fixed amount of immobilized yeast is packed in a fermentor and a substrate solution is supplied to said fermentor so that it runs parallel with the immobilized yeast, thereby effecting a continuous alcohol fermentation.

(B) Description of the Prior Art

Alcohol (ethyl alcohol) is widely used for not only drinking but also various industrial purposes, and is manufactured by fermentation methods and synthesis methods. In the manufacture of alcohol on an industrial scale according to a fermentation method, where molasses is used as the starting material, part of said molasses is first diluted with hot water to such an extent as its total sugar content becomes about 15 wt./V%, a nutrient is added thereto, then the pH thereof is adjusted, and the same is sterilized. After completion of said sterilization, the same is cooled to about 30° C., and then is inoculated with yeast fungus and cultured for about 2 days to prepare a seed culture (seed yeast). On the other hand, the remainder of said molasses is diluted with hot water to such an extent as its total sugar content becomes about 25 wt./V%, then the aforesaid seed yeast is added thereto, and thus fermentation is conducted at about 30° C. The fermentation is completed in about 4 days and about 13 vol.% alcohol is prepared. Successively, the yeast is removed from the obtained alcohol broth and the latter is distilled to obtain alcohol (ethyl alcohol).

However, the fact is that the aforesaid manufacture of alcohol according to ferementation method is conducted in a batch culture, and that said batch culture includes drawbacks or disadvantages, for instance: (1) Since the yeast concentration is in a low range such as 3-4 g/l, a large fermentor capacity is needed in order to produce alcohol in a desired amount; (2) Since the reaction speed is slow, the fermentation time is prolonged and consequently the productivity is decreased, (3) Since the alcohol and the other by-products strongly retard the reaction speed, the concentration of product alcohol is naturally reduced from the viewpoint of manufacturing alcohol economically, and the like.

In order to solve these problems and profitably carry out the manufacture of alcohol according to a fermentation method, there have been proposed various methods, for instance, conducting the manufacture of alcohol continuously while dispersing yeast in a substrate solution, preparing an immobilized yeast by immobilizing a living yeast on a carrier and utilize this immobilized yeast in a living or growing state, and so forth.

The alcohol fermentation method using this immobilized yeast has been proposed very recently. A continuous alcohol manufacturing method is disclosed which comprises supplying a glucose-containing nutritional medium to an immobilized yeast obtained by immobilizing a concentrated yeast (*Saccharomyces carbergensis*) with carrageenan, or a concentrated yeast (*Saccharomyces cerevisiae*) with polyacrylamide (see "Kagaku Kozyo" (Chemical Factories) vol. 23, No. 3, pp. 26-30 published by Nikkan Kogyo Shinbun Sha).

The continuous culture to be practiced without immobilizing yeast as above mentioned, namely, while dispersing yeast in a substrate solution, and the continuous culture using immobilized yeast may be expected to be more profitable than the conventional batch culture in that alcohol can be manufactured in a relatively short time and consequently the fermentor can achieve a high volumetric efficiency (alcohol productivity of fermentor per unit volume and unit time). Among these continuous culture methods it is considered that the continuous culture using an immobilized yeast is more profitable.

SUMMARY OF THE INVENTION

The inventors have earnestly devoted themselves to studies and investigations on the packing characteristic at the time when an immobilized yeast is packed into a fermentor, the behavior of carbonic acid gas caused by the progress of fermentation, the behavior of insoluble components in a molasses material and so forth in order to carry out the alcohol fermentation process using an immobilized yeast more efficiently, and consequently have found that the aforesaid alcohol fermentation can be effected very smoothly by specifying the configuration and fermentation operation of the immobilized yeast to be used in the present invention. The present invention has been completed on the basis of this finding.

As can be inferred from the aforegoing, the object of the present invention is to provide a continuous alcohol fermentation process using immobilized yeast which is suitable for conducting alcohol fermentation with high efficiency.

In other words, the continuous alcohol fermentation process according to the present invention is characterized in that a filmy immobilized yeast is packed in a fermentor in a packing fraction of 65% or less, said filmy immobilized yeast being obtained by immobilizing a yeast having an alcohol producing activity on a carrier; a substrate solution is continuously supplied to said fermentor so that said substrate solution may run parallel with the immobilized yeast, thereby effecting alcohol fermentation; and then a product alcohol is separated from the resulting fermentation liquid (alcohol broth) and recovered.

DETAILED DESCRIPTION OF THE PREFERRED EMBODIMENTS OF THE INVENTION

Figure 1:
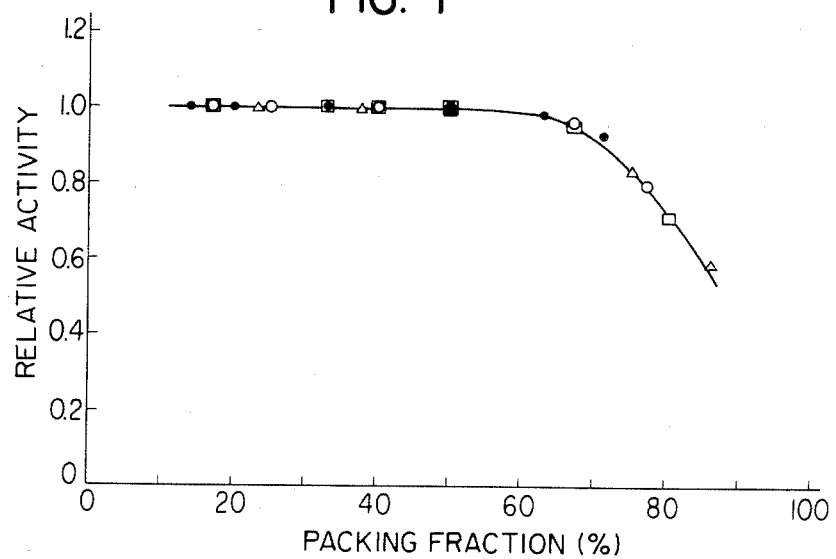
FIG. 1 is a graph illustrating the relation between the relative activity and the packing fraction of the immobilized yeast used in the process of the present invention.

The yeast used in the process of the present invention may be roughly said to be in an immobilized one formed in a filmy state. As the immobilized yeast there can be utilized any one which has an alcohol producing activity and has been immobilized, while living, on a carrier and which can be used in a living or growing state. Accordingly, as examples of the immobilized yeast as aforesaid there can be enumerated those obtained by entrapping and immobilizing a yeast on a carrier (for instance: polyacrylamide, polyvinyl alcohol, photo-crosslinked resin, agar, carrageenan, collagen or the like) and by adhering a yeast on a carrier.

When carrageenan, agar or the like is employed as a carrier, an intended immobilized yeast can be obtained by thermally dissolving a fixed amount of a carrier as referred to above in water; cooling the resulting solution to thereby obtain an aqueous solution; mingling a fixed amount of yeast with said aqueous solution; further cooling this mixture to cause gelation; and then forming the resulting gel into a desired shape. When collagen is employed as a carrier, an intended immobilized yeast may be obtained by swelling and solubilizing, for instance, oxhide powder, with an alkaline amine solution, adding a yeast liquid to the thus treated oxhide powder and mixing; spreading the resulting mixed solution onto a flat plate and air-drying same; and thereafter treating the same with glutaraldehyde or the like thereby to form it into a desired shape. Moreover, in case polyacrylamide is employed as a carrier, an intended immobilized yeast may be obtained by adding, to a fixed amount of yeast-containing solution, acrylamide monomer, crosslinking agent (for instance: N,N'-methylenebisacrylamide), polymerization promotor (for instance: dimethylaminopropionitrile) and polymerization initiator (for instance: potassium persulfate) for polymerizing purposes; then cooling this to cause gelation; and thereafter forming the resulting gel into a desired shape.

The immobilized yeast suitably used in the process of the present invention includes one prepared by immobilizing a yeast on a carrier using radiation, besides those methods enumerated above. This immobilized yeast can be prepared for instance by mingling a fixed amount of yeast liquid with an aqueous polyvinyl alcohol solution; pouring this mixed solution into an ampoule; subjecting the same to radioactive rays (100,000–1,000,000 Rad/hr) to cause gelation; and then forming the resulting gel into a desired shape. The immobilized yeast may also be prepared by mingling a photo-crosslinked resin (a hydrophilic unsaturated compound which has an average molecular weight of 300–80,000 and includes two or more photo-polymerizable ethylenic unsaturated radicals in one molecule) with an aqueous yeast suspension; subjecting the resulting mixed solution to irradiation by active rays (250–6,000 Å); and forming the thus obtained immobilized matter into a desired shape.

The photo-crosslinked resin used herein includes polyesters, i.e. reaction products between unsaturated polybasic acids (maleic anhydride and the like) and polyhydric alcohols; polyesters, i.e., reaction products between polyethylene glycols and (metha)acrylic acid; unsaturated urethanes, nonionic unsaturated acrylic resin, anionic unsaturated acrylic resin, cationic unsaturated acrylic resin, unsaturated polyvinyl alcohol, unsaturated celluloses, unsaturated polyamides, unsaturated epoxys having an acid value of 40–200 and the like.

The preparation of the immobilized yeast having a desired shape may be made by (1) first immobilizing a yeast and then forming the immobilized yeast into a desired shape as referred to above or (2) for instance, pouring a solution of a mixture of carrier material and yeast in a container or the like having an intended shape and thereafter immobilizing said solution, thereby obtaining an immobilized yeast having a desired shape as soon as its immobilization is completed. These measures may be selected properly taking into consideration the shapes intended and immobilizing methods to be employed. Furthermore, if an intended shape requires it, one can insert reinforcements, for instance, such as wire gauze, filter cloth, high molecular compound and the like upon immobilizing or molding.

The yeast usable in the present invention may be any one which has an alcohol producing activity. As typical examples thereof there may be enumerated Saccharomyces, Zygosaccharomyces, Schizosaccharomyces and the like. As some substantial and preferable yeasts there will be cited *Saccharomyces formosensis, Saccharomyces cerevisiae, Saccharomyces carlsbergensis, Saccharomyces robustus, Saccharomyces rouxii, Zygosaccharomyces japonicus, Zygosaccharomyces majar, Zygosaccharomyces soya, Schizosaccharomyces pombo, Schizosaccharomyces octosporus, Schizosaccharomyces mellacei* and the like.

The shape of the immobilized yeast may be roughly classified into a granular form or a film form. According to the investigation results of the inventors it is proved that when a packing layer type fermentor is employed, it is profitable to use films of immobilized yeast rather than the granular yeast, so that the former is allowed to be parallel with the flow of liquid (substrate solution or fermentation liquid). The reason why this is profitable is not completely clear, but it may be considered as follows.

The use of granular immobilized yeast (which will be abridged as "granule" for convenience) gives rise to problems such as (1) when the flow speed of liquid within a fermentor is increased there is caused fluid pressure which deforms granules and consequently brings about excessive contact between granules. Due to this, the void fraction within the fermentor and the surface area of granules decrease, and further the pressure loss within the fermentor increases. As a result, the coefficient of mass transfer between the liquid and granules is lowered and thus the alcohol fermentation activity is deteriorated. Accordingly, it is inevitably required to narrow the range of operation to an undue extent in order to remove the aforesaid disadvantage. (2) Since the carbonic acid gas arising from the yeast with the advance of alcohol fermentation comes to flow with the liquid, the resulting gas pressure acts to further advance the tendency revealed in the preceding problem (1), and (3) the effective surface area of granules is decreased because various kinds of fine impurities contained in the material for alcohol fermentation deposit between granules and adhere to the surfaces of granules.

On the other hand, when a film of immobilized yeast is packed in a fermentor so as to be parallel with the flow of liquid there can be found the following advantages (1') the immobilized yeast is scarcely subjected to fluid pressure and therefore the state as-packed can be maintained for a long period of time; (2') the carbonic acid gas generated at the time of alcohol fermentation moves with the flow of liquid and contacts the immobilized yeast only at the film surface, whereby the immobilized yeast is negligibly affected by gas pressure; and (3') the impurities contained in the material move with the flow of liquid and thus do not readily deposit within the fermentor, whereby a highly efficient alcohol fermentation can be expected.

For these reasons, it is possible for the process of the present invention to employ any mode of film immobilized yeast which can be packed in the fermentor so that it may be parallel with the flow of liquid. Accordingly, the immobilized yeast may be utilized in the manner, for instance, of (a) a plurality of sheet-like immobilized yeasts are arranged parallel at suitable intervals therebetween in the fermentor, (b) an immobilized yeast is made circinate with suitable intervals or (c) a plurality of both end-opened tubular (cylindrical, many-sided tubular or the like) immobilized yeasts are concentrically arranged at suitable intervals therebetween. The preceding (a) and (b) are intended for practical purposes taking into consideration easiness of molding and easiness of packing in the fermentor.

The thickness of the immobilized yeast is suitably in the range of about 0.1–3 mm, but may vary depending on the property of the immobilized yeast to be used.

Regarding the structure of the fermentor, there can be employed any one which is adapted for packing the aforesaid immobilized yeasts so that the latter may be parallel with the flow of liquid, but in order to allow the liquid to flow as uniformly as possible, it is preferable to adopt one by which immobilized yeasts can be packed in the fermentor while leaving fixed intervals therebetween.

In packing the immobilized yeasts in this fermentor, it is necessary to adjust the operation conditions so that the immobilized yeasts may be used effectively, namely the packed immobilized yeasts can exhibit their activity to the full. This requirement may be achieved by increasing the linear speed of the liquid so as to reduce the influence of liquid-film diffusion resistance created on the surfaces of immobilized yeasts when the substrate contained in the solution permeates into the immobilized yeasts. The aforesaid linear speed can be increased by reducing the sectional area of the fermentor or elevating the packing fraction by narrowing the distance between immobilized yeasts (by narrowing the packing distance between immobilized yeasts).

In the case of alcohol fermentation, however, there is no necessity of elevating the packing fraction extremely by narrowing the packing distance between immobilized yeasts as referred to above because the carbonic acid gas generated with the progress of the alcohol fermentation reaction brings about turbulence in the liquid and rather acts to reduce the influence of the liquid-film diffusion resistance onto the surfaces of immobilized yeasts and further because the reaction speed is so slow in the case of the alcohol fermentation that the influence of the liquid-film diffusion resistance on the surfaces of immobilized yeasts is reduced.

When the packing fraction is increased by narrowing the packing distance as aforesaid, it further brings about a disadvantageous state concerning the reaction speed of alcohol fermentation because the carbonic acid gas generated with the progress of the fermentation reaction brings out the unreacted substrate solution to the outside of the system and because the turbulent liquid flow caused by the aforesaid carbonic acid gas acts to retard the reaction speed. Still further, it should not be profitable to narrow the aforesaid packing distance to an extreme degree because it complicates the operation of packing the immobilized yeast and further insoluble components contained as impurities in the material are liable to deposit.

In particular, as is clear from the relation between relative activity and packing fraction per unit immobilized yeast illustrated in FIG. 1, there is found a tendency that the relative activity per unit immobilized yeast denotes a constant such as 1.0 irrespective of the thickness of immobilized yeast when the packing fraction is about 65% or less, but the aforesaid relative activity lowers due to the influence of the turbulent liquid flow caused by the carbonic acid gas as referred to above when the packing fraction is in excess of the above limit. The term "relative activity" used herein denotes activities per unit immobilized yeast at respective packing fractions relative to the activity per unit immobilized yeast (which is taken as 1.0) where the immobilized yeasts have respective thickness and the packing fraction is 50%.

It can be seen from this fact that in order to permit the immobilized yeast to exhibit the activity to the fullest and to keep it up, it is necessary to pack the immobilized yeast so that the packing fraction of immobilized yeast may be maintained at a value up to about 65% at most, that is, about 65% or less during the reaction (see FIG. 1).

It is desired for industrial applications that the reaction should be conducted at a packing fraction which is also desirable from the viewpoint of the volumetric efficiency for the fermentor. As is understood from the relation between the relative volumetric efficiency and the packing fraction of immobilized yeast illustrated in FIG. 2, it is found that the relative volumetric efficiency rises as the packing fraction of immobilized yeast increases and reaches the maximum of 1.0 when said packing fraction is about 50%, and thereafter lowers as the aforesaid packing fraction further increases. The term "relative volumetric efficiency" used herein denotes volumetric efficiencies at respective packing fractions relative to the volumetric efficiency per unit immobilized yeast (which is taken as 1.0) where the immobilized yeasts have respective thickness and the packing fraction is 50%. Accordingly, although two points having the same relative volumetric efficiency value exist, one greater and one less than the packing fraction of about 50%, of these two points the one of lower packing fraction is preferable because it can economize the amount of immobilized yeast used.

Due to this, it is desirable from the viewpoint of industrial applications that the immobilized yeast should have a packing fraction which can be expected to attain a practically available relative volumetric efficiency of about 0.3 or more, preferably a relative volumetric efficiency of about 0.5 or more, more preferably a relative volumetric efficiency of about 0.6 or more.

Judging these factors (the relative activity and relative volumetric efficiency of unit immobilized yeast) collectively, it is found that the packing fraction of immobilized yeast is preferably in the range of 10% or more and 65% or less, and within said range, preferably 15–65%, more preferably 20–65%.

The dimensions of the immobilized yeast used in the process of the present invention may be determined optionally, and therefore there is no necessity of determining the dimensions specifically. In this instance, however, a fermentor of dimensions sufficient for packing the immobilized yeast so that it can maintain the aforesaid packing fraction range and can be arranged to be parallel with the flow of the substrate solution, whose dimensions are for instance about 1000 mm long, 1000 mm wide and 1000 mm high, is called one unit. This unit may be disposed in the plural according to the dimensions of the fermentor to be actually used or may be piled in multistages as occasion demands.

The actual practice of alcohol fermentation using the immobilized yeast may be carried as follows. First, a nutritional salt-containing sugar solution material (for instance, such as grape sugar solution, refined sugar solution, beet molasses solution or blackstrap molasses solution) is diluted with hot water or the like to a fixed sugar concentration and thereafter is subjected to a sterilization step and thermally sterilized. The thermally sterilized sugar solution is cooled to a temperature of 30°-32° C. This cooled solution is continuously supplied from one port to a fermentor packed previously with the immobilized yeast so that said sugar solution may run parallel with the immobilized yeast. The sugar solution and the yeast are allowed to contact with each other for a fixed time for fermentation and then a broth is withdrawn continuously from another port. The withdrawn broth is separated and recovered in accordance with the usual manner and there is obtained a refined product alcohol. It is preferable to install a cooling means within the fermentor for the purpose of maintaining a temperature suitable for alcohol fermentation therewithin.

As mentioned above, the process of the present invention comprises packing the specifically shaped immobilized yeast in the fermentor so that it may be parallel with the flow of the substrate solution to be introduced and a specific packing fraction may be maintained, and introducing the substrate solution in the fermentor arranged as above to thereby achieve a continuous alcohol fermentation. According to the process of the present invention, the impurities contained in the fermentation material have difficulty depositing and the retarding influence of the alcohol can be minimized. Therefore, the process of the present invention permits the immobilized yeast packed within the fermentor to maintain its activity to the fullest and further can answer strong expectations for achieving alcohol fermentation with high volumetric efficiency.

The present invention will be explained in more detail with reference to the Example referred to hereinafter. In this connection, it is to be noted that every part used in the Example is part by weight.

EXAMPLE

Figure 2:
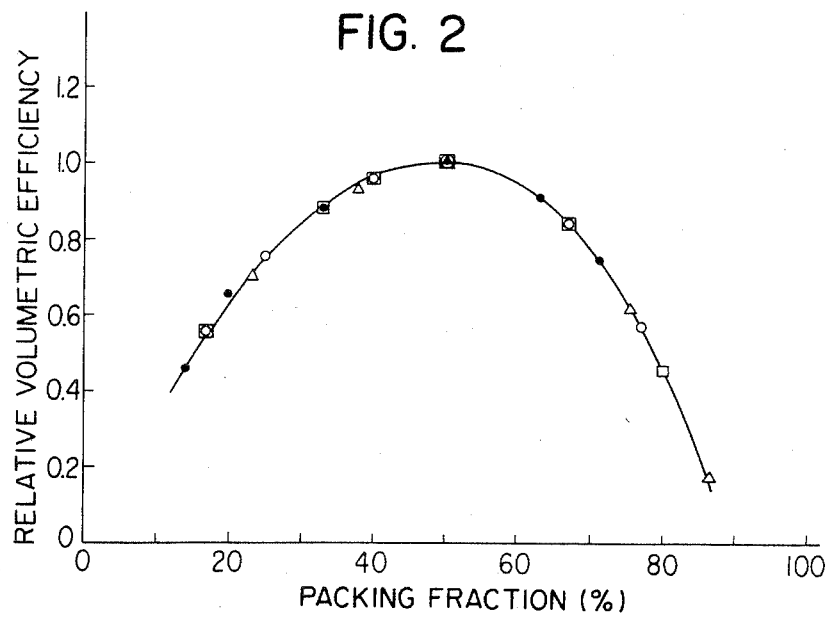
FIG. 2 is a graph illustrating the relation between the relative volumetric efficiency and the packing fraction according to the process of the present invention.

*Saccharomyces formosensis* was subjected to shake culture treatment in a molasses a medium (the sugar concentration thereof was 20 wt./V%). After the growth of this yeast has been confirmed, it was recovered by means of a centrifugal separator to thereby prepare a suspension thereof. 50 parts of a urethanated prepolymer (average molecular weight: about 5000) comprising 2000 g of polyethylene glycol (average molecular weight: about 4000), 1 mol (222 g) of isophoronediisocyanate and 1 mol (130 g) of 2-hydroxyethyl methacrylate were taken and dried to the aforesaid suspension and 0.5 part of benzoinethyl ether (photosensitizer). This mixture was dispersed uniformly by means of a homogenizer. In this instance, the amount of the yeast suspension added was set so that the initial yeast concentration at the subsequent immobilizing step might amount to 5% by weight. Subsequently, the thus prepared dispersion was poured in a 200 mm long and 200 mm broad frame provided with 1.0 mm thick spacers on a polypropylene film (50μ thick) spread on a glass plate and the same was covered with a polypropylene film (50μ thick) to prevent the air from entering thereinto. This was subjected to irradiation of light from a low pressure mercury lamp (3600 Å) to thereby obtain an about 1.0 mm-thick film of immobilized yeast. In the same manner there were obtained films of immobilized yeasts having thicknesses of about 0.5 mm, about 2.0 mm and about 3.0 mm respectively by the use of 0.5 mm-thick, 2.0 mm-thick, and 3.0 mm-thick spacers respectively. The thus obtained filmy immobilized yeasts were cut into dimensions of 50 mm long and 200 mm wide and thicknesses of about 0.5 mm, about 1.0 mm, about 2.0 mm and about 3.0 mm. These filmy immobilized yeasts were each packed in a fermentor having the dimensions of 50 mm long, 50 mm wide and 200 mm high and the packing distance was adjusted by means of a spacer so as to attain a packing fraction in the range of 14–86%. A series of alcohol fermentations were carried out under the conditions: reaction temperature 30° C., pH 5.0 and packing fraction as enumerated in Table-1, in the manner of making a molasses culture (whose sugar concentration is 25 wt./V%) flow parallel with the film of immobilized yeast. The amount of the culture supplied in this instance was set to 50 ml/hr. The alcohol fermentation progressed with the passing of time and the alcohol concentration reached a stable state after about 80 hours. The alcohol concentrations at this time are as shown in Table-1. The activity and volumetric efficiency per unit immobilized yeast evaluated on the basis of the obtained result are as shown in Table-1. FIG. 1 and FIG. 2 represent respectively the relative activities and relative volumetric efficiencies per unit immobilized yeast at respective packing fractions for the actitivies and volumetric efficiencies per unit immobilized yeast having the respective thicknesses shown in Table-1 when the packing fraction of 50% is taken as 1.0. In this connection, it is to be noted that in these drawings, the symbol o represents the case where the thickness of immobilized yeast is about 1.0 mm, the symbol represents the case where the thickness of said yeast is about 0.5 mm, the symbol □ represents the case where the thickness of the yeast is about 2.0 mm, and the symbol Δ does the case where the thickness of the yeast is about 3.0 mm respectively.

TABLE 1

| Thickness of filmy immobilized yeast (mm) | Packing fraction (%) | Concemtration of product alcohol (g/l) | Activity per unit* immobilized yeast ($\frac{\text{g-ethanol}}{\text{ml resin hr}}$) | Volumetric efficiency ($\frac{\text{Kg ethanol}}{\text{m}^3 \text{ fermentor hr}}$) |
|---|---|---|---|---|
| About 0.5 | 71 | 69.0 | 0.052 | 6.9 |
|  | 63 | 84.5 | 0.055 | 8.45 |
|  | 50 | 93.0 | 0.056 | 9.3 |
|  | 33 | 82.0 | 0.056 | 8.2 |
|  | 20 | 60.0 | 0.056 | 6.0 |
|  | 14 | 42.5 | 0.056 | 4.25 |
| About 1.0 | 77 | 51.5 | 0.043 | 5.15 |
|  | 67 | 75.5 | 0.052 | 7.55 |
|  | 50 | 90.0 | 0.054 | 9.0 |
|  | 40 | 86.5 | 0.054 | 8.65 |
|  | 25 | 67.5 | 0.054 | 6.75 |
|  | 17 | 49.5 | 0.054 | 4.95 |

TABLE 1-continued

| Thickness of filmy immobilized yeast (mm) | Packing fraction (%) | Concemtration of product alcohol (g/l) | Activity per unit* immobilized yeast $\left(\dfrac{\text{g-ethanol}}{\text{ml resin hr}}\right)$ | Volumetric efficiency $\left(\dfrac{\text{Kg ethanol}}{\text{m}^3 \text{ fermentor hr}}\right)$ |
|---|---|---|---|---|
| About 2.0 | 80 | 31.5 | 0.030 | 3.15 |
|  | 67 | 58.0 | 0.040 | 5.8 |
|  | 50 | 70.0 | 0.042 | 7.0 |
|  | 40 | 67.0 | 0.042 | 6.7 |
|  | 33 | 61.5 | 0.042 | 6.15 |
|  | 17 | 38.0 | 0.042 | 3.8 |
| About 3.0 | 86 | 9.5 | 0.019 | 0.9 |
|  | 75 | 33 | 0.027 | 3.3 |
|  | 50 | 53 | 0.032 | 5.3 |
|  | 37.5 | 49.5 | 0.032 | 4.95 |
|  | 23 | 37.0 | 0.032 | 3.7 |

*The activity per unit immobilized yeast is a value calculated in terms of the reaction speed which is free from retard caused by ethanol.

What is claimed is:

1. A continuous fermentation process for producing ethanol, utilizing a fermentation vessel through which liquid is adapted to flow in one direction, which comprises the steps of:

packing inside said fermentation vessel thin film means having a thickness of from 0.1 to 3 mm and containing immobilized living yeast so that the surfaces of said thin film means extend in said direction of liquid flow in said vessel, from 10 to 65% of the volume of said fermentation vessel is occupied by said thin film means and opposing surfaces of laterally adjacent portions of said thin film means are substantially parallel with and spaced from each other to provide elongated parallel passages therebetween, said passages extending in said direction of liquid flow and being parallel with the surfaces of said thin film means, said thin film means consisting essentially of immobilized living yeast mixed in an organic, film-forming, photo-crosslinked, resin carrier, said thin film means having been prepared by mixing an aqueous yeast suspension with photo-crosslinkable resin and then subjecting the thus-formed mixture to radiation having a wavelength of from 250 to 6000 Å to photo-crosslink said resin, said yeast being capable of fermenting a fermentable, carbohydrate-containing, substrate liquid to form an ethanol-containing, fermented liquid; flowing a fermentable, carbohydrate-containing, substrate liquid through said fermentation vessel and through said passages in said direction of liquid flow so that said liquid substrate flows in parallel with and contacts the surfaces of said thin film means, under conditions and for a period of time effective to cause said substrate liquid to be fermented to form an ethanol-containing fermented liquid and so that impurities and carbon dioxide gas generated by the fermentation travel with the liquid in said direction of liquid flow; discharging the fermented liquid from said discharge opening and recovering ethanol from said fermented liquid.

2. A process according to claim 1, wherein said thin film means occupies from 20 to 65% of the volume of said fermentation vessel.

3. A process according to claim 1, wherein said thin film means is a plurality of parallel, laterally spaced-apart films packed in said fermentation vessel.

4. A process according to claim 1, wherein said film means is a plurality of parallel, concentric, open-ended tubes packed in said fermentation vessel.

5. A process as claimed in claim 1 in which said photo-crosslinkable resin is selected from the group consisting of unsaturated polyesters, unsaturated urethanes, nonionc unsaturated acrylic resin, anionic unsaturated acrylic resin, cationic unsaturated acrylic resin, unsaturated polyvinyl resin, unsaturated celluloses, unsaturated polyamides and unsaturated epoxy resins having an acid value of 40 to 200.

6. A process as claimed in claim 1 in which said photo-crosslinkable resin is a hydrophilic unsaturated resin having an average molecular weight of 300 to 80,000 and having two or more photopolymerizable ethylenically unsaturated radicals in the molecule.

7. A process as claimed in claim 1 in which said photo-crosslinkable resins is a mixture of a urethanated prepolymer prepared from polyethylene glycol, isophorone diisocyanate and 2-hydroxyethyl methacrylate, and a photo-initiator.

* * * * *